United States Patent [19]

Komives et al.

[11] Patent Number: 4,708,733

[45] Date of Patent: Nov. 24, 1987

[54] HERBICIDAL 4-CHLORO-ARYLOXY-ACETYL- AND 4-CHLORO-ARYLOXY-PROPIONYL-MALONATES

[75] Inventors: Tamás Komives, Budapest; Ferenc Dutka, Budapest; István Barta, Paty; István Jablonkai, Budapest; Ágnes Hulesch, Budapest; Ferenc Bihari, Budapest; Gyula Eifert, Dunaharaszti; Péter Bohus, Budapest; Mihály Nagy, Budapest; György Bácskai, Budapest; Istvan Kuronya, Budapest, all of Hungary

[73] Assignees: Budapesti Vegyimuvek; MTA Kozponti Kemiai I Kutato Intezet, both of Budapest, Hungary

[21] Appl. No.: 910,736

[22] Filed: Sep. 23, 1986

[30] Foreign Application Priority Data

Oct. 1, 1985 [HU] Hungary .............................. 3799/85
Jun. 27, 1986 [HU] Hungary .............................. 3799/85

[51] Int. Cl.$^4$ ..................... A01N 43/40; A01N 31/14; C07D 213/64; C07C 69/612
[52] U.S. Cl. ......................................... 71/94; 546/302; 560/53; 71/108; 71/109
[58] Field of Search ................... 546/302; 71/94, 108, 71/109; 560/53

[56] References Cited

PUBLICATIONS

March, J. Adv. Org. Chem., 2nd Ed., pp. 441–442.

Primary Examiner—Henry R. Jiles
Assistant Examiner—J. Richter
Attorney, Agent, or Firm—Karl F. Ross; Herbert Dubno; Jonathan Myers

[57] ABSTRACT

The invention relates to new 4-chloro-aryloxy-acetyl- or 4-chloro-aryloxy-propionyl-malonates of the general Formula I,

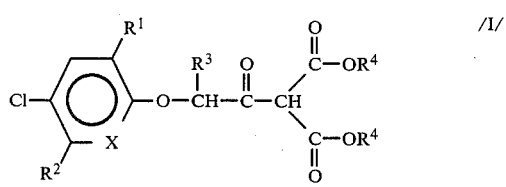

a process for the preparation thereof and herbicidal compositions comprising the same.

In the general Formula I
$R^1$ stands for chlorine or methyl;
$R^2$ represents hydrogen or chlorine;
$R^3$ stands for hydrogen or methyl;
$R^4$ represents $C_{1-4}$ alkyl and the two $R^4$ groups may be identical or different; and
X is —N= or —CH=.

The compounds of the general Formula I may be prepared by reacting a compound of the general Formula II

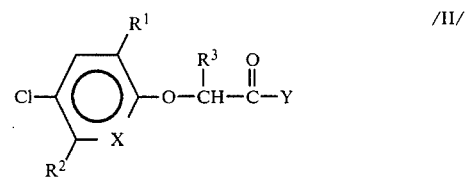

with a metal derivative of a malonate of the general Formula III;

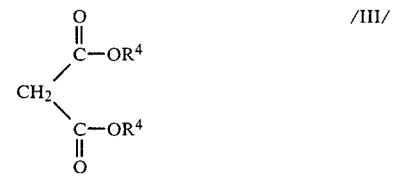

or in the presence of an metal compound with a malonate of the general Formula III; or by reacting a compound of the general Formula IV

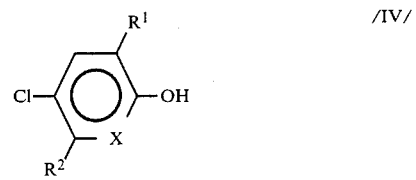

with a compound of the general Formula V

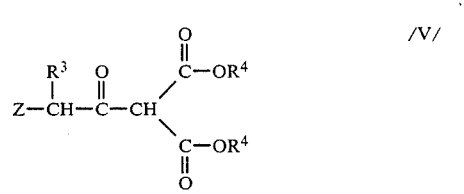

(in which Formulae $R^1$, $R^2$, $R^3$, $R^4$ and X are as stated above; Z stands for halogen and Y represents halogen, cyano or alkylcarbonyloxy).

The new compounds of the general Formula I possess valuable herbicidal properties.

5 Claims, No Drawings

HERBICIDAL 4-CHLORO-ARYLOXY-ACETYL- AND 4-CHLORO-ARYLOXY-PROPIONYL-MALONATES

This invention relates to new 4-chloro-aryloxy-acetyl- and 4-chloro-aryloxy-propionyl-malonates, a process for the preparation thereof, herbicidal compositions comprising the same and a method for combating weeds by using said compositions.

It is known that certain aryloxy-alkane-carboxylic acid derivatives show herbicidal properties. Such compounds are disclosed in French Pat. No. 1,186,520 and U.S. Pat. Nos. 2,523,228 and 2,543,397.

According to an aspect of the present invention there are provided new compounds of the Formula I

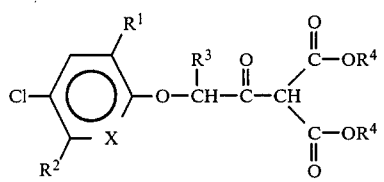

wherein
$R^1$ stands for chlorine or methyl;
$R^2$ represents hydrogen or chlorine;
$R^3$ stands for hydrogen or methyl;
$R^4$ represents $C_{1-4}$ alkyl and the two $R^4$ groups may be identical or different; and
X is $-N=$ or $-CH=$.

The new compounds of the Formula I differ from the known derivatives in the moiety attached to the carbonyl group.

The new compounds of the Formula I exhibit a significantly stronger herbicidal effect than the known derivatives, particularly in pre-emergent application. The new compounds of the Formula I may be used advantageously in various cultures—particularly in maize—for the control of broad-leaved weeds—as opposed to the known derivatives the compounds of the present invention do not cause any damage to the cultivated plants at the herbicidal dose.

A preferred compound of the Formula I is the derivative in which
$R^1$ is chlorine;
$R^2$ and $R^3$ represent hydrogen;
$R^4$ is ethyl and
X stands for $-CH=$.

In a further preferred representative of the compounds of the Formula I
$R^1$ and $R^3$ represent methyl;
$R^2$ is hydrogen,
$R^4$ stands for ethyl and
X is $-CH=$.

The term "$C_{1-4}$ alkyl" relates to straight or branched chain alkyl groups having 1-4 carbon atoms (e.g. methyl, ethyl, n-propyl isopropyl, n-butyl).

According to a further aspect of the present invention there are provided herbicidal compositions comprising as active ingredient in an amount of 0.001-95% by weight a compound of the Formula I with suitable inert solid and/or liquid carriers or diluents and optionally with further auxiliary agents (e.g. surfactants, antifoaming, antifreezing and adhesive agents).

The compositions of the present invention may be solid or liquid and may be finished in usual forms (e.g. powder mixture, dusting powder, granules, paste, emulsion, suspension, solution, spray, concentrate etc.). The compositions comprise diluents and carriers and auxiliary agents generally used in agriculture and plant protection.

The solid carriers may be mineral or synthetic materials e.g. China-clay, siliceous earth, talc, attapulgite, diatomaceous earth, alumina, silicic acid and various silicates. As liquid diluent e.g. mineral oil fractions (e.g. gas oil, or kerosine), oils of animal or vegetable origin, aromatic, aliphatic or alicyclic hydrocarbons (e.g. benzene, toluene, xylene, cyclohexane, tetrahydro naphthalene) and derivatives thereof (e.g. chlorobenzene, alkyl naphthalenes, cyclohexanol, butanol) or strongly polar solvents (e.g. dimethyl formamide, dimethyl sulfoxide, N-methyl-prolidone, water) may be used.

The surfactants (emulsifying, dispersing, wetting, antifoam or antiaggregating agents) may be of ionic or non-ionic character. As ionic surfactants the following compounds may be used: salts of saturated or unsaturated carboxylic acids, sulfonates of aliphatic, aromatic or aliphatic-aromatic hydrocarbons; sulfonates of alkyl, aryl and aralkyl alcohols; sulfonates of alkyl, aryl and aralkyl carboxylic acids and esters and ethers thereof; sulfonates of condensation products of phenols, cresols or naphthalene; sulfatated oils of animal or vegetable origin; alkyl, aryl or aralkyl phosphate esters; sulfonates and phosphates of polyglycol ethers of ethylene oxide formed with fatty alcohols or alkyl phenols.

As non-ionic surfactants e.g. the following compounds may be used: condensation products of ethylene oxide formed with fatty alcohols; alkyl aryl polyglycol ethers; polymers of ethylene oxide and/or propylene oxide and derivatives thereof; alkyl cellulose.

As antifoam agents e.g. ethylene oxide/propylene oxide condensation products having a low molecular weight; aliphatic alcohols; special silicone oils or fatty acid amides may be used.

As adhesive or thickening agent e.g. alkaline earth metal soaps; salts of sulfosuccinic acid esters; or natural or synthetic macromolecular materials which are soluble or swellable in water may be used.

As antifreezing agent e.g. ethylene glycol, propylene glycol or glycerol may be used.

The herbicidal compositions of the present may be prepared by known methods of pesticidal industry by admixing at least one compound of the Formula I with suitable inert solid and/or liquid carriers or diluents an optionally with auxiliary agents.

According to a still further aspect of the present invention there is provided a method for controlling weeds which comprises applying onto the objects to be protected—preferably onto plants, parts of plants or soil—an effective amount of a compound of the Formula I or a composition comprising the same.

According to a still further aspect of the present invention there is provided a process for the preparation of compounds of the formula I which comprises (a) reacting a 4-chloro-aryloxy-alkane carboxylic acid derivative of the Formula II

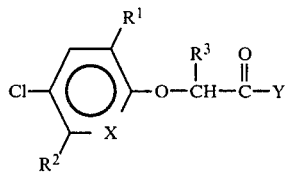

wherein above and Y represents halogen, cyano or $C_{1-6}$ alkyl-carbonyloxy with a metal derivative of a malonate of the Formula III

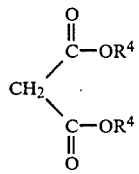

or in the presence of a metal compound—preferably magnesium chloride—with a malonate of the Formula III; or (b) reacting a hydroxy aromatic compound of the Formula IV

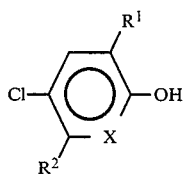

or an alkali metal salt thereof with a malonate of the Formula V

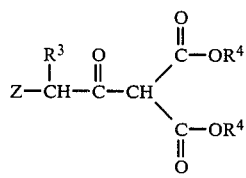

Z represents halogen.

According to process (a) it is preferred to use a sodium, potassium or magnesium derivative the malonate of the Formula III. If the malonic acid derivative of the general Formula III is used per se it is preferred to carry out the reaction in the presence of magnesium compound particularly magnesium chloride as metal compound. The reaction may be carried out preferably in an inert solvent. As solvent advantageously a hydrocarbon (e.g. benzene, toluene or xylene), an ether (e.g. diethyl ether, 1,2-dimethoxy ethane, tetrahydrofuran or dioxan) an amide (e.g. dimethyl formamide, hexamethyl phosphoric acid triamide) a ketone (e.g. acetone or diethyl ketone) or a nitrile (e.g. acetonitrile) may be used.

The malonic acid derivatives of the Formula III are reacted in the form of a metal salt thereof with the compound of the Formula II. The metal salts of the malonates may be prepared previously, e.g. by reacting a malonate of the Formula III with an alkali or alkaline earth metal compound. According to an other alternative the reaction of the compounds of the Formula II and III is carried out in the presence of a metal compound—preferably magnesium chloride. In this case the metal salt of the malonate of the Formula III is in situ formed in the reaction mixture.

The reaction may be accomplished at a temperature between $-10°$ C. and $+180°$ C., preferably at $30°-100°$ C. The desired compound is separated by known methods after the removal of the by-products formed.

The malonates of the Formula III and metal salts thereof and the starting materials of the Formula II are partly known compounds. Such compounds are disclosed in U.S. Pat. No. 2,223,228 and in the publications Org. Synth. Coll. Vol. IV, 285 and J. Org. Chem. 50, 2622 (1965). The new compounds of the Formula II may be prepared in an analagous manner to the process described in the said publications.

According to process (b) the compounds of the Formulae IV and V are reacted preferably in the presence of an inert solvent or diluent. As reaction medium the solvents disclosed above in connection with process (a) may be used. It is preferred to work in the presence of an acid binding agent, e.g. an alkali hydroxide, alkali carbonate, alkali ethylene or alkali tert.butylate (preferably sodium or potassium hydroxide, carbonate, ethylate or tert.butylate) or any suitable organic base (e.g. triethyl amine).

Further details of the present invention are to be found in the following Examples without limiting the scope of protection to said Examples.

EXAMPLE 1

Preparation of diethyl-2',4'-dichloro-phenoxy-acetyl-malonate (a) A 50% etheral solution of 24 g of 2',4'-dichloro-phenoxy-acetyl-chloride is added dropwise under stirring to a mixture of diethyl-ethoxy-magnesium malonate prepared from 17.6 g of diethyl malonate and 50 ml of ether. The addition of the acid chloride having been completed the reaction mixture is heated to boiling for an hour, cooled to room temperature and washed successively with 100 ml of 5% sulfuric acid, 100 ml of a 6% sodium bicarbonate solution and 100 ml of water. The etheral phase is evaporated, the excess of the malonate is distilled off and the residue is taken up in 100 ml of benzene. This mixture is subjected to chromatography on a column containing 20 g of silica and the column is washed with 50 ml of benzene. The united eluates are evaporated. Thus 31 g of the pale yellow crystalline desired compound are obtained, yield 85%, mp.: $110°-115°$ C.

(b) Into a 500 ml flask equipped with a stirrer and a dropping funnel 9.52 g of anhydrous magnesium chloride and 100 ml of anhydrous acetonitrile are weighed in. To the hetergeneous mixture 16.0 g of diethyl malonate are added. The reaction flask is placed into an ice bath and 20 ml of triethyl amine are added. To the solution 23.9 g of 2',4'-dichloro-phenoxy-acetyl chloride are added at 0° C. under stirring within 15 minutes. The reaction mixture is stirred at 0° C. for an hour and at room temperature for 12 hours whereupon it is cooled to 0° C. and 60 ml of a 5M hydrochloric acid solution is added. The solution thus obtained is extracted three times with 100 ml of ether each, the united extracts are dried over magnesium sulfate and the solvent and the traces of diethyl malonate are removed. The residual pale yellow oil slowly solidifies on standing. Thus 32.7 g of the desired compound are obtained, yield 91%, mp.: $110°-115°$ C.

EXAMPLE 2

Preparation of dimethyl-2'-methyl-4'-chloro-phenoxy-acetyl-malonate

A 50% etheral solution of 26 g of 2'-methyl-4'-chlorophenoxy-acetyl bromide is added dropwise to a mixture of dimethyl-ethoxy-magnesium malonate prepared from 14.5 g of dimethyl malonate and 50 ml of ether. When the addition of the acid bromide is completed the reaction mixture is heated to boiling for an hour and the reaction mixture is worked up as described in Example 1. Thus 25 g of the desired compound are obtained in the form of a viscous oil which solidifies to pale yellow crystals on standing, yield 81%, mp.: 70°–74° C.

EXAMPLE 3

Preparation of diethyl-2-(2',4'-dichlorophenoxy)-propionyl-malonate

A mixture of 25 g of 2-(2',4'-dichloro-phenoxy)-propionyl chloride and 30 ml of ether is added dropwise to a 35% etheral solution of magnesium-diethyl malonate prepared from 17.6 g of diethyl malonate. When the addition of the acid chloride is completed the reaction mixture is heated to boiling for an hour and worked up as described in Example 1. Thus 29 g of the desired compound are obtained in the form of a yellow oil, yield 76%, $n_D^{25}=1,355$.

EXAMPLE 4

Preparation of diethyl-2-(2'-methyl-4-chloro-phenoxy)-propionyl-malonate (a) Into a 200 ml round-bottomed flask equipped with a magnetic stirrer, a thermometer, a dropping funnel and a calcium chloride tube 100 ml of toluene, 10.1 g of triethyl amine and 21 g of 2-(2'-methyl-4'-chloro-phenoxy)-propionic acid are weighed in. The reaction mixture is cooled under 0° C. and 10.8 g of ethyl chloro formiate are added dropwise at such a rate that the temperature should be between −1° C. and 0° C. The thick suspension formed is stirred for a further period of 20 minutes, whereupon a mixture of diethyl-ethoxy-magnesium-malonate prepared from 17.6 g of diethyl malonate and 50 ml ether is added dropwise at such a rate that the temperature should not exceed 0° C. The reaction mixture is allowed to stand at room temperature for 16 hours and worked up as described in Example 1. Thus 31 g of the desired compound are obtained in the form of a pale yellow oil, yield 88%, $n_D^{25}=1.348$.

(b) 25.1 g of diethyl-2-chloro-propionyl-malonate and 14.2 g of 4-chloro-o-cresol are dissolved in 100 ml dimethyl formamide. The mixture is stirred at 60° C. for 48 hours in the presence of 13.8 g of potassium carbonate. The reaction mixture is filtered and the filtrate is evaporated. The residue is dissolved in 100 ml of benzene and washed successively with 100 ml of a saturated aqueous sodium bicarbonate solution and 100 ml of water. The benzene phase is evaporated to yield 28 g of the desired compound, yield 80%.

(c) A mixture of 25.1 g of diethyl-2-chloro-propionyl-malonate, 16.5 g of sodium 4-chloro-2-methyl-phenolate and 100 ml of dimethyl formamide is stirred at 60° C. for 48 hours. The reaction mixture is filtered and the filtrate is evaporated. The residue is dissolved in 100 ml of benzene and washed succesively with 100 ml of a saturated aqueous sodium bicarbonate solution and 100 ml of water. The benzene layer is evaporated to give 28.7 g of the desired compound, yield 82%.

EXAMPLE 5

Preparation of diethyl-2-(2',4',5'-trichloro-phenoxy)-propionyl-malonate

One proceeds in an analogous manner to Example 4 except that 27 g of 2-(2',4',5'-trichloro-phenoxy)-propionic acid are reacted first with 12 g of pivaloyl chloride and thereafter with diethyl-ethoxy-magnesium malonate prepared from 17.6 g of diethyl malonate. The reaction mixture is worked up. Thus 37 g of the desired compound are obtained in the form of pale yellow crystals, yield 91%, mp.: 62°–66° C.

EXAMPLE 6

Preparation of dimethyl-2-(3',5',6'-trichloro-2-pyridyloxy)-propionyl-malonate

A solution prepared from 4.6 g of sodium, 26 g of dimethyl malonate and 60 ml of ether is added dropwise to a mixture of 28 g of 2-(2',4',5'-trichloro-2-pyridyloxy)-propionyl chloride and 50 ml of ether. The reaction mixture is heated to boiling for 2 hours and worked up as described in Example 1. Thus 26 g of the desired compound are obtained in the form of pale yellow crystals, yield 71%, mp.: 53°–57° C.

EXAMPLE 7

Preparation of methyl-propyl-2-(2',4',5'-trichloro-phenoxy)-propionyl malonate 27 g of 2-(2',4',5'-trichloro-phenoxy)-propionic acid are reacted in an analogous manner to Example 4(a) at first with 12 g of pivaloyl chloride and thereafter with methyl-propyl-ethoxy-magnesium malonate prepared from 17.6 g of methyl-propyl malonate. The reaction mixture is worked up. Thus 37 g of the desired compound are obtained in the form of a pale yellow crystals, yield 91%, mp.: 60°–64° C.

PREPARATION OF HERBICIDAL COMPOSITIONS

EXAMPLE 8

Granules having an active ingredient content of 0.01%

2.3 g of technical grade compound No. 1 (purity 89%) are dissolved in 97.7 g of methylene chloride to yield a solution of a concentration of 2% by weight. An acidic pearl siliceous earth carrier prepared from 4000 g of diatomaceous earth are placed into a Loedige 20 type turbine stirrer; the average particle size of the carrier is between 0.5 and 2 mm. 20 g of the active ingredient premix (2% mm/m solution) are sprayed onto the granulated carrier throught Tee-Jet 10080 nozzles at a rate of 5 g/minutes, whereby the granules are stirred in the Loedige type stirrer with a velocity of 50 r.p.m. The sorption type granules are packed.

EXAMPLE 9

Sprayable powder having an active ingredient of 95%

240 g of compound No. 2 (purity 97%; previously powdered in a mill equipped with a rotating blade) are admixed with 2.5 g of Cab-O-Sil M5 amorphous silica; carrier) and 7.5 g of type 1494 dispersing agent (sodium salt of the condensation product of sulfonated cresole and formaldehyde) in a mortar. The powdered mixture is ground in a turbine mill (Alpine LMRS-80) under an injected air pressure of 5 bar and a grinding air pressure of 4.5 bar at a feeding rate of 250 g/h. Although the sprayable powder thus obtained contains no separate wetting agent it is readily wettable, and has a maximal particle size of 20 μm. In a spray of a concentration of 10 g/l the floatability at 30° C. after 30 minutes is as follows:

84% in CIPAC standard D water; and
91% in CIPAC standard A water.

EXAMPLE 10

Emulsifiable concentrate with an active ingredient content of 24%

40 g of Tween 85 (ethoxylated sorbitane trioleate) and 30 g of Sapogenat T-180 (ethoxylated tributyl phenol) emulsifiers and 250 g of technical grade compound No. 4 (purity: 96%) are dissolved in 400 g of cyclohexanone at 40°-45° C. under stirring. When all the components are dissolved the solution of the active ingredient (temperature 40°-45° C.) is poured into a mixture of 200 g of ion-exchanged water and 70 g of ethylene glycol under vigorous stirring whereupon the mixture is cooled to 15°-20° C. Before the termination of the stirring period 10 g of Silicon S RE antifoam agent (a 30% emulsion of dimethyl silicone oil) are added to the emulsion and five minutes later the stirring is stopped.

EXAMPLE 11

Biological application of the composition

Grass seeds and seeds of cultivated plants are sown into sand of the river Danube in plastic boxes (size 10×10×10 cm) and compositions prepared from the emulsifiable concentrates of the test compounds are sprayed onto the surface of the sand (pre-emergent treatment) and three weeks after sowing (post-emergent treatment). The plastic boxes are watered at a rate required for normal plant growth and are kept in a glass house. The results of the treatment are evaluated after a test period of four weeks and evaluated with the aid of a scale from 0 to 10, wherein 0=n symptoms and 10=completely destroyed infected plants (100%).

As reference compounds two commercially available herbicides are used, namely mecocrop (chemical name: 2-84′-chloro-2′-methyl-phenoxy)-propionil acid) and 2,4-D (chemical name: 2,4-dichloro-phenoxy-acetic acid).

The results are summarized in Table I. It appears from the said data that the activity of the compounds of the present invention—as the average activity against grassy weeds—is superior to that of the reference compounds, particularly in pre-emergent application.

The tolerance of a number of cultivated plants against the compositions of the present invention has been determined by means of the methods of treatment disclosed in this Example. It has been found that dicotyledonous cultivated plants tolerate well all the compositions of the present invention and in the herbicidal dose none of the invention compounds cause any phytotoxical symptoms.

TABLE I

Herbicidal activity of the compounds of the general Formula I against various weeds in several cultivated plant cultures in pre-emergent and post-emergent treatment.

| Test compound Example No. | Dose kg active ingredient/ha | AM pre | AM post | CH pre | CH post | SI pre | SI post | AB pre | AB post | GA pre | GA post | maize pre | maize post | Autumn wheat pre | Autumn wheat post | sorghum pre | sorghum post |
|---|---|---|---|---|---|---|---|---|---|---|---|---|---|---|---|---|---|
| 1 | 0.5 | 8 | 8 | 8 | 8 | 8 | 8 | 6 | 5 | 4 | 6 | 0 | 1 | 0 | 0 | 0 | 0 |
|   | 1.5 | 10 | 10 | 10 | 10 | 10 | 10 | 9 | 10 | 8 | 8 | 0 | 1 | 2 | 0 | 1 | 1 |
| 2 | 0.5 | 8 | 8 | 8 | 8 | 8 | 8 | 8 | 6 | 4 | 6 | 0 | 1 | 0 | 0 | 0 | 0 |
|   | 1.5 | 10 | 10 | 10 | 10 | 10 | 10 | 10 | 10 | 9 | 8 | 0 | 2 | 0 | 0 | 0 | 0 |
| 3 | 0.5 | 8 | 8 | 8 | 8 | 7 | 7 | 7 | 8 | 7 | 7 | 0 | 1 | 0 | 0 | 0 | 0 |
|   | 1.5 | 10 | 10 | 10 | 10 | 10 | 10 | 10 | 10 | 10 | 10 | 0 | 2 | 0 | 0 | 0 | 0 |
| 4 | 0.5 | 8 | 8 | 8 | 8 | 8 | 8 | 8 | 8 | 8 | 8 | 0 | 1 | 0 | 0 | 0 | 0 |
|   | 1.5 | 10 | 10 | 10 | 10 | 10 | 10 | 10 | 10 | 10 | 10 | 0 | 2 | 0 | 0 | 0 | 0 |
| 5 | 0.5 | 6 | 6 | 7 | 7 | 10 | 10 | 9 | 8 | 4 | 4 | 0 | 1 | 0 | 1 | 0 | 1 |
|   | 1.5 | 9 | 9 | 9 | 9 | 10 | 10 | 10 | 10 | 9 | 9 | 0 | 2 | 1 | 2 | 1 | 1 |
| 6 | 0.5 | 6 | 6 | 6 | 6 | 7 | 8 | 8 | 8 | 8 | 8 | 0 | 1 | 0 | 1 | 0 | 1 |
|   | 1.5 | 9 | 9 | 9 | 9 | 10 | 10 | 10 | 10 | 10 | 10 | 0 | 2 | 1 | 2 | 1 | 1 |
| 7 | 0.5 | 7 | 6 | 6 | 7 | 9 | 10 | 10 | 9 | 5 | 4 | 0 | 1 | 0 | 1 | 0 | 1 |
|   | 1.5 | 10 | 9 | 8 | 9 | 10 | 10 | 10 | 10 | 9 | 10 | 0 | 2 | 1 | 2 | 1 | 1 |
| MCPP | 0.5 | 2 | 3 | 2 | 3 | 5 | 6 | 2 | 5 | 4 | 6 | 3 | 3 | 0 | 0 | 0 | 0 |
|   | 1.5 | 4 | 8 | 4 | 8 | 9 | 10 | 4 | 8 | 6 | 8 | 6 | 6 | 1 | 0 | 2 | 0 |
| 2,4-D | 0.5 | 1 | 3 | 2 | 3 | 5 | 6 | 2 | 5 | 2 | 2 | 2 | 1 | 0 | 0 | 0 | 0 |
|   | 1.5 | 4 | 8 | 5 | 9 | 6 | 10 | 4 | 8 | 3 | 3 | 3 | 2 | 1 | 0 | 2 | 0 |

AM = *Amaranthus retroflexus*, CH = *Chenopodium album*, SI = *Sinapis arvensis*, AB = *Ambrosia elatior*, GA = *Galium aparine*

What we claim is:

1. A compound of the Formula (I)

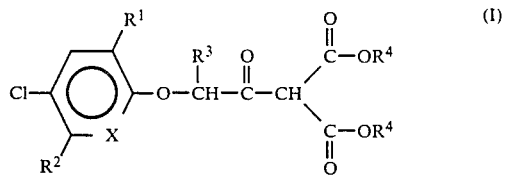

wherein
$R^1$ is chloro or methyl;
$R^2$ is hydrogen or chloro;
$R^3$ is hydrogen or methyl
$R^4$ is $C_1$ to $C_4$ alkyl and the two $R^4$ groups may be identical or different; and
X is —N= or —CH=.

2. The compound of the Formula (I) defined in claim 1 wherein $R^1$ is chloro, $R^2$ and $R^3$ are each hydrogen, $R^4$ is ethyl, and X is —CH=.

3. The compound of the Formula (I) defined in claim 1 wherein $R^1$ and $R^3$ are each methyl, $R^2$ is hydrogen, $R^4$ is ethyl, and X is —CH=.

4. A herbicidal composition which comprises as active ingredient a herbicidally effective amount of the compound of the Formula (I) defined in claim 1 in admixture with an agriculturally inert carrier.

5. A method for controlling weeds which comprises the step of applying to a plant site a herbicidally effective amount of the compound of the Formula (I) defined in claim 1.

* * * * *